United States Patent [19]

Jackman

[11] 3,956,694

[45] May 11, 1976

[54] TEST TABLE FOR MAGNETIC PARTICLE FLAW DETECTION

[76] Inventor: Arthur A. Jackman, R.D. No. 2, Corry, Pa. 16407

[22] Filed: Apr. 23, 1975

[21] Appl. No.: 570,681

Related U.S. Application Data

[63] Continuation of Ser. No. 445,840, Feb. 26, 1974, abandoned, which is a continuation-in-part of Ser. No. 347,469, April 3, 1973, abandoned.

[52] U.S. Cl. ............................................. 324/38
[51] Int. Cl.² ..................................... G01R 33/12
[58] Field of Search .................................. 324/38

[56] References Cited

UNITED STATES PATENTS

| | | | |
|---|---|---|---|
| 2,217,733 | 10/1940 | DeForest | 324/38 |
| 2,277,431 | 3/1942 | Fitch | 324/38 |

FOREIGN PATENTS OR APPLICATIONS

| | | | |
|---|---|---|---|
| 441,604 | 1/1936 | United Kingdom | 324/38 |
| 735,880 | 8/1955 | United Kingdom | 324/38 |

Primary Examiner—Robert J. Corcoran
Attorney, Agent, or Firm—Charles L. Lovercheck

[57] ABSTRACT

A table top, table frame and tank combination. The table top has a flat topped surface made of a rectangular steel plate. Insulating bars are supported on the table top and extend radially from the center and a bar made of an electrical conductor is supported on each of the insulating members providing a space for magnetic flux to flow therebetween. The table frame is made up of four angle irons that are welded together at the corners to form a frame and an angle iron leg is attached to each corner. One leg of each angle iron lays in a common plane with one leg of each other angle iron, defining a flat surface designed to hold the different sizes of table tops in required position. A fluid tank for the purpose of containing a fluid to be pumped to the part to be inspected is supported below the frame. This apparatus can be used with any equipment of the type generally used for magnetic testing capable of producing the proper magnetizing current.

1 Claim, 4 Drawing Figures

U.S. Patent  May 11, 1976  Sheet 1 of 2  3,956,694
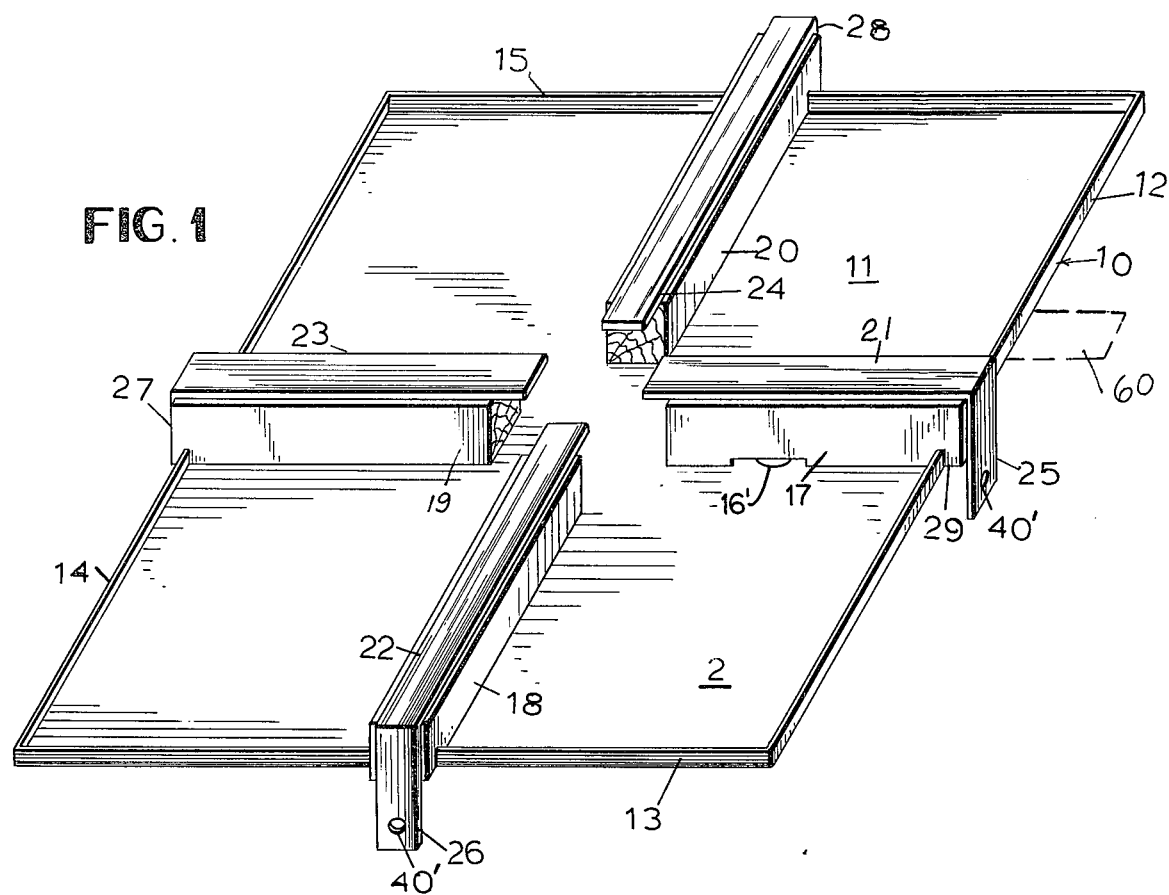
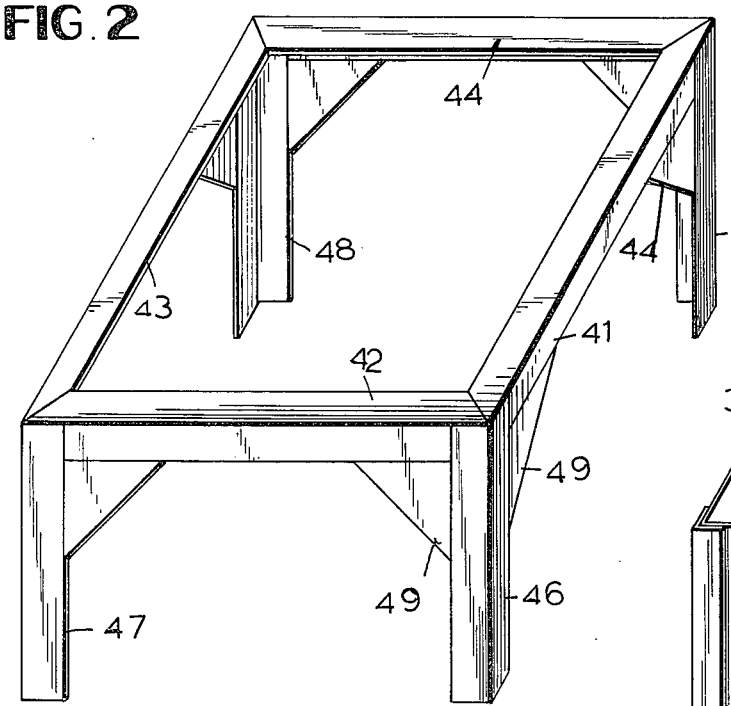
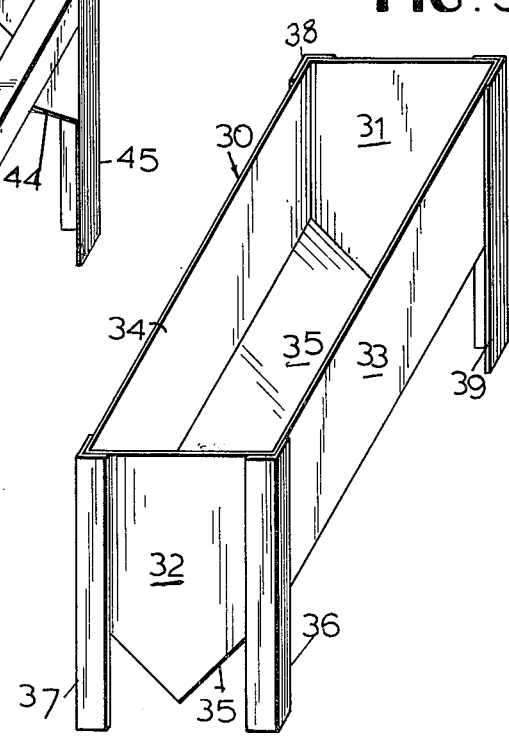

TEST TABLE FOR MAGNETIC PARTICLE FLAW DETECTION

REFERENCE TO RELATED APPLICATION

This application is a continuation of application Ser. No. 445,840 filed Feb. 26, 1974, which in turn was a continuation-in-part of application Ser. No. 347,469, filed on Apr. 3, 1973 both now abandoned.

REFERENCE TO PRIOR ART

Patents showing magnetic testing equipment of the general type disclosed herein are shown in British Pat. No. 735,880, U.S. Pat. No. 2,217,733, and U.S. Pat. No. 2,277,431.

GENERAL STATEMENT OF INVENTION

This invention relates to inspection apparatus and more particularly to apparatus designed for introducing magnetism into material and performing a magnetic particle inspection.

OBJECTS OF THE INVENTION

It is an object of the invention to provide an improved testing table.

Another object of the invention is to provide a table top consisting of a flat plate built up on the sides to contain any fluid material in this area. There is also a drain hole for removing any excess material and four insulator blocks for the purpose of insulating the four conductor bars from the table top.

Another object of the invention is to provide a table frame that is designed to hold the different sizes of table tops in the required position.

Another object of the invention is to provide a table top, table frame and fluid tank in combination for the purpose of containing any fluid to be pumped to the part to be inspected.

Another object of the invention is to provide an apparatus that can be used with any equipment capable of producing proper magnetizing current made up of a combination of table top, table frame and fluid tank.

Another object of the invention is to provide equipment designed to allow the inspection of large rings and other shapes with a minimum of handling and setup time and result in a greater degree of safety for the equipment and operators.

With the above and other objects in view, the present invention consists of the combination and arrangement of parts hereinafter more fully described, illustrated in the accompanying drawings and more particularly pointed out in the appended claims, it being understood that changes may be made in the form, size, proportions, and minor details of construction without departing from the spirit or sacrificing any of the advantages of the invention.

GENERAL DESCRIPTION OF THE DRAWINGS

FIG. 1 is an isometric view of the table top according to the invention.

FIG. 2 is an isometric view of the table frame.

FIG. 3 is an isometric view of the fluid tank.

DETAILED DESCRIPTION OF THE DRAWINGS

Figure 4:
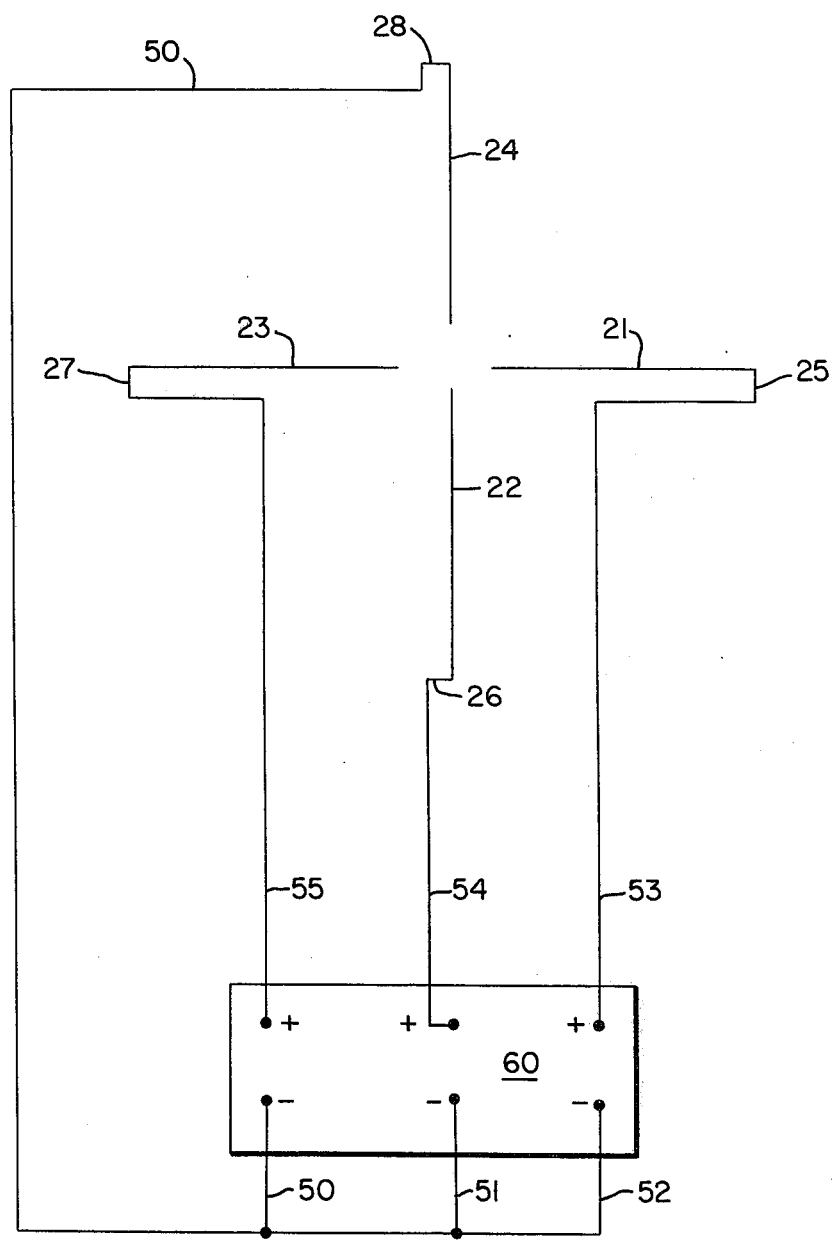
FIG. 4 shows a wiring diagram for connecting a source of power to the conductor bars.

Now with more particular reference to the drawings, the table top is indicated generally at 10, made up of a flat steel plate having a top surface 11 and marginal edges 12, 13, 14 and 15 formed by a flange that may be welded to the plate and forms an enclosure for suitable fluid. Drain hole 16' is formed in the plate and this drain hole may drain excess fluid or liquid material into the tank 30. The table top may rest on the table frame 40 above the tank 30, held in place by its weight.

The insulator blocks 17, 18, 19 and 20 are supported on the table top and conductor bars 21, 22, 23, and 24 are supported on the insulator blocks. Each conductor bar has a downwardly extending end bar 25, 26, 27 and 28, spaced outwardly from the table. The end bars are attached to the respective conductor bars and extend downwardly past the lower surface of the table top 11. Each insulator block 17, 18, 19 and 20 is notched at 29 to receive the respective marginal edge 12, 13, 14 or 15, thereby holding the bar on its top spaced from the table. The notches 29 are spaced from the ends of the insulators so that an insulation space is formed between the bars 25, 26, 27 and 28 and the marginal edges 12, 13, 14 or 15 of the table.

Holes 40' are formed in the ends of bars 25, 26, 27 and 28. Holes 40' may be used for connecting electrical conductors from a suitable source of direct current power.

The tank 30 has ends 31 and 32 and sides 33 and 34 and downwardly inclined bottom surfaces 35 converge at the bottom. Legs 36, 37, 38 and 39 are in the form of angle irons that receive the corners of the tank between the legs of the angle irons.

The table frame is made up of a rectangular frame; angle irons 41, 42, 43 and 44 welded together form corners with one leg of each angle iron having its upward surface laying in a common plane with the others so that the table top 11 may rest on the top surface. The legs 45, 46, 47 and 48 are made in the form of angle irons and they receive the corners of the table between the legs of the angle irons. The gusset plates 49 reinforce the legs.

The proper field of magnetism is supplied to the work by electric current flowing in the work. The work to be tested can be supported on the bars 21, 22, 23 and 24 and a suitable liquid can be placed in the space defined by the marginal flanges 12, 13, 14 and 15. A suitable circulating pump P will pump the liquid from the tank 30 to the table top.

The magnetic testing device to be used with the apparatus disclosed is indicated generally at 60. The magnetic testing apparatus produces three sources of direct current isolated electrically from each other, and is of a type familiar to those skilled in the art and of the general type shown in U.S. Pat. No. 2,277,431. A single source of direct current could be used having the negative terminal connected to one of the conductor bars and the other terminal connected in sequence to each of the other three bars. A selector switch of a type familiar to those skilled in the art could be used for this purpose. There are three separate sources of direct current in the example shown. These separate sources each have their negative terminal connected to end bar 28. These negative terminals are indicated by 50, 51 and 52. The positive terminals of these sources are connected to end bars 25, 26, and 27 by means of conductors 53, 54 and 55. A copper mesh pad, or other flexible electrical conducting material familiar to those skilled in the art, may be laid over the top of conductor bars 21, 22, 23 and 24, to make an efficient electrical connection between the bars and the work. A large steel ring or wheel to be tested can then be laid on top of the mesh material and the electric current from the conductor bars flowing from the bar 24 to bars 26, 27 and 28 will provide a magnetic field around the test piece which will act on the liquid being pumped from tank 30 to the wheel supported on the bars 21, 22, 23 and 24. The liquid containing the magnetic material in suspension will form patterns on the wheel or ring which will show by inspection whether or not there are defects in the wheel or ring being inspected.

The foregoing specification sets forth the invention in its preferred practical forms but the structure shown is capable of modification within a range of equivalents without departing from the invention which is to be understood is broadly novel as is commensurate with the appended claims.

I claim:

1. An apparatus for magnetic particle inspection of structures of the type of rings of magnetic material of various sizes to determine cracks comprising
   a relatively flat table top, having upwardly extending marginal edges forming a container for liquid and a drain hole positioned therein,
   at least four elongated blocks made of insulating material extending from a central position radially outward beyond said marginal edge,
   said elongated blocks being generally rectangular in cross section and having flat tops and flat bottoms resting on said table top substantially throughout their entire length, each said insulating block having an upwardly extending notch adjacent its outer end receiving said upwardly extending edge marginal of said table top,
   at least four conductor bars made of electrically conducting material,
   each said bar being generally rectangular in cross section and having a flat top and a flat bottom resting on one of said flat tops of said insulating blocks throughout substantially its entire length,
   said bars extending from a central position radially outward to a position to the outer end of the said blocks on which the respective bar rests,
   a downwardly extending conducting end bar generally rectangular in cross section and of equal width to the said bars fixed to each said conductor bar and extending downwardly therefrom beyond the lower edge of said table top,
   a hole means in the lower ends of each said end bars for connecting an electrical conductor to said end bar,
   the inner ends of said conductor bars being spaced from each other and spaced from said table top,
   the top surface of said conductor bars being relatively flat and disposed in a common plane with each other whereby an object having at least one planar surface can be supported thereon in electric conducting relation thereto,
   a tank positioned under said table and proximate said drain hole to collect liquid passing through said hole,
   means for pumping liquid containing magnetic particles from said tank onto the test piece positioned upon said conductor bars, and
   D.C. current means connected to said bars to pass current through the test piece to create a magnetic field therein, said field being distorted by flaws, whereby magnetic particles in the liquid will be attracted thereto to indicate the flaws.

* * * * *